United States Patent

Spona et al.

[11] Patent Number: 5,980,940
[45] Date of Patent: *Nov. 9, 1999

[54] PHARMACEUTICAL COMBINATION PREPARATION FOR HORMONAL CONTRACEPTION

[75] Inventors: Jürgen Spona, Vienna, Austria; Bernd Düsterberg, Berlin, Germany

[73] Assignee: Schering AG, Berlin, Germany

[ * ] Notice: This patent is subject to a terminal disclaimer.

[21] Appl. No.: 08/930,630

[22] PCT Filed: Apr. 4, 1996

[86] PCT No.: PCT/EP96/01529

§ 371 Date: Jan. 27, 1998

§ 102(e) Date: Jan. 27, 1998

[87] PCT Pub. No.: WO96/32114

PCT Pub. Date: Oct. 17, 1996

[30] Foreign Application Priority Data

Apr. 8, 1995 [DE] Germany .................. 195 13 662

[51] Int. Cl.⁶ .................. A61K 31/57; A61K 31/56
[52] U.S. Cl. .................. 424/464; 514/177; 514/178; 514/170; 514/182; 514/843; 514/173
[58] Field of Search .................. 424/465, 464; 514/177, 178, 170, 182, 843, 173

[56] References Cited

U.S. PATENT DOCUMENTS

| | | |
|---|---|---|
| 3,502,772 | 3/1970 | Ijzerman . |
| 4,921,843 | 5/1990 | Pasquale . |
| 5,280,023 | 1/1994 | Ehrlich et al. . |
| 5,583,129 | 12/1996 | Spona . |
| 5,633,242 | 5/1997 | Oettel et al. . |
| 5,756,490 | 5/1998 | Lachnit et al. . |

*Primary Examiner*—Thurman K. Page
*Assistant Examiner*—Brian K. Seidlech
*Attorney, Agent, or Firm*—Millen, White, Zelano & Branigan

[57] ABSTRACT

The invention provides a pharmaceutical combination preparation with two hormone components in a packaging unit and intended for time-sequential oral administration, comprising a number of daily dosage units physically separate and individually removable in the packaging unit, whereby as a hormonal active ingredient a first hormone component contains in combination an estrogen preparation and in at least a dosage that is sufficient to inhibit ovulation a gestagen preparation, and as a hormonal active ingredient the second hormone component contains only an estrogen preparation, whereby the first hormone component comprises 23 or 24 daily units and the second hormone component comprises 4, 3 or 2 daily units, and between these two hormone components, 2 or 1 active ingredient-free daily units are present or 2 or 1 blank pill days are indicated, and the total number of hormone daily units and the active ingredient-free daily units or the blank pill days is equal to the total number of days of the desired cycle, but at least 28 days in length. This combination preparation is useful for female birth control, and allows for an estrogen content that is as low as possible in each individual dosage unit and also has a low total hormone content per administration cycle, with high contraceptive reliability, low incidence of follicular development, and satisfactory cycle control, with reliable avoidance of intracyclic menstrual bleeding as well as of undesirable side-effects.

10 Claims, No Drawings

PHARMACEUTICAL COMBINATION PREPARATION FOR HORMONAL CONTRACEPTION

This application is a 371 of PCT/EP96/01529, filed on Apr. 4, 1996.

DESCRIPTION

This invention relates to a pharmaceutical combination preparation with two hormone components which are manufactured physically separately in a packaging unit and are intended for oral administration that is sequential in time and which consist in each case of a number of physically separate and individually removable daily dosage units placed in the packaging unit, whereby as a hormonal active ingredient a first hormone component contains in combination an estrogen preparation and, in a dosage that is sufficient at least to inhibit ovulation, a gestagen preparation in either one-stage or multi-stage structuring and as a hormonal active ingredient the second hormone component contains only an estrogen preparation, whereby the first hormone component comprises 23 or 24 daily units and the second hormone component comprises 4, 3 or 2 daily units; and between these two hormone components, 2 or 1 active ingredient-free daily units (placebos) are present or 2 or 1 blank pill days are indicated, and the total number of hormone daily units and the active ingredient-free daily units or the blank pill days is equal to the total number of days of the desired cycle, but at least 28-days in length, and a corresponding packing that contains this combination preparation.

Oral contraceptives in the form of combination preparations have been known as so-called one-phase preparations since 1960. These preparations consist of 21 active ingredient-containing dosage units and 7 active ingredient-free tablets or coated tablets. The daily dosage unit consists of an estrogen and a gestagen. In one-phase preparations, the dose of the active substance that is to be administered daily is equally high in each dosage unit. If the dose of the active components that is to be administered daily is different in the individual dosage units in individual sections over the administration cycle, these are so-called multi-phase preparations. Triquilar® can be cited as an especially well-known representative (DE-A 23 65 103).

It was possible to reduce the daily gestagen dosage continuously through the development of new, more effective gestagens than those contained in the first oral contraceptives. It was also possible to lower the daily estrogen dosage, although in most cases ethinylestradiol is still contained as an estrogen in hormonal contraceptives.

Because of the development of new, improved oral contraceptives, the following three points were (and are) emphasized:

(1) Contraceptive reliability,
(2) good cycle control, i.e., low incidence of intracyclic menstrual bleeding and
(3) a minimum of undesirable side-effects are to be ensured.

Contraceptive reliability is mainly provided by the gestagen component. The amount of its daily dosage corresponds in each case to at least the maximum dose that is considered necessary for the gestagen in question to inhibit ovulation. The ethinylestradiol that is used in most cases as an estrogen in combination preparations is supposed to increase the ovulation-inhibiting effect of the gestagen and mainly to ensure cycle stability. The daily dose in the case of ethinylestradiol administered alone, which must be used to inhibit ovulation, is 100 µg.

Combination preparations with the most recent generation of gestagens are, e.g., the one-phase preparation Femovan (DE-PS 2546062) or Marvelon (DE-OS 2361120). Milvane® can be mentioned (EP-0 148 724) as an example of a multi-phase preparation whose dosage units contain a gestagen of the most recent generation, namely gestodene. In the case of these three-phase preparations, in most cases 4–6 coated tablets are administered in the first phase, in which each coated tablet contains an amount of estrogen in a low dose and a gestagen in a low dose. In the second phase of 4–6 coated tablets, each dosage unit contains an estrogen at a dose that is equal or slightly raised, increased to a maximum up to 2-fold, and a gestagen at a dose that is equal or slightly raised, increased to a maximum up to 1.5-fold. In a third phase of 9–11 units, each coated tablet contains an estrogen at a dose that is equal or is again lowered, reduced to a maximum of the initial value, and a gestagen at a dose that is further raised, increased to a maximum of 3 times the initial value. Then come 7 pill-free days.

Recently, multi-phase combination preparations were also proposed which can provide an extended, i.e., up to 24-day, intake of active ingredient-containing dosage units in a 28-day cycle. In this case, the daily gestagen-dosage amount either increases from the first through the second to the third phase (EP-A 0 491 415), or it decreases (EP-A 0 491 438). To complete the 28-day cycle, in the first case 4 blank pill days, 4 placebos, or else 4 exclusively gestagen-containing dosage units follow, or in the second case 4 to 7 blank pill days or 4 to 7 placebos follow.

The purpose of the development of new oral contraceptives with a reduced daily hormone dose was to minimize the side-effects that are described in epidemiological studies. Recent epidemiological data point to such a trend toward better compatibility of low-dosed preparations with respect to cardiovascular side-effects. [Thorogood M., Oral Contraceptives and Cardiovascular Disease: An Epidemiologic Overview; Pharmacoepidemiology and Drug Safety, Vol. 2: 3–16 (1993); Gerstman, B. B.; Piper, J. M.; Tomita, D. K.; Ferguson, W. J.; Stadel, B. V.; Lundin, F. E.; Oral Contraceptive Estrogen Dose and the Risk of Deep Venous Thromboembolic Disease, Am J E, Vol. 133, No. 1, 32–36 (1991); Lidegaard O, Oral Contraception and Risk of a Cerebral Thromboembolic Attack: Results of a Case-Control Study: BMJ Vol. 306, 956–63 (1993); Vessey, M.; Mant, D.; Smith, A.; Yeates, D., Oral Contraceptives and Venous Thromboembolism: Findings in a Large Prospective Study; BMJ, Vol. 292, (1986); Mishell, D. R., Oral Contraception: Past, Present and Future Perspectives; Int J Fertile, 36 Suppl., 7–18 (1991)].

A correlation between the amount of the daily estrogen dose and the frequency of cardiovascular complications is assumed.

The preparation with the lowest-dosed amount of estrogen at this time is marketed as Mercilon® and contains 20 µg of ethinylestradiol in combination with 150 µg of desogestrel in each daily dosage unit over 21 days, followed by a 7-day pill-free interval. The cycle control of this preparation is somewhat less good than that of preparations with a higher estrogen dose. The observation, confirmed in several studies, of slighter ovarian suppression for the preparation that contains 20 µg of ethinylestradiol represents another clinically important problem. Obviously, for many women this very low estrogen dose can result in the maturation of follicles, as has been detected in ultrasound studies or hormone studies [Lunell, N. O.; Carlström, K.; Zador, G., Ovulation Inhibition with a Combined Oral Contraceptive Containing 20 μg of Ethinylestradiol and 250 μg of Levonorgestrel; Acta Obstet Gynecol Scand Suppl. 88: 17–21 (1979); Mall-Haefeli, M.; Werner-Zodrow, I.; Huber, P. R., Klinische Erfahrungen mit Mercilon und Marvelon unter besonderer Berucksichtigung der Ovar-Funktion [Clinical Experiments with Mercilon and Marvelon with Special Consideration of Ovarian Function]; Geburtsh. und Frauenheilk. [Childbirth and Gynecology], 51, 35–38, Georg Thieme Verlag, Stuttgart-New York (1991); Strobel, E., Behandlung mit oralen Kontrazeptiva [Treatment with Oral Contraceptives]; Fortschr. Med. 110 Jg. No. 20 (1992); Letter to Editor, Contraception 45: 519–521 (1992); Teichmann, A. T.; Brill, K., Can Dose Reduction of Ethinylestradiol in OCs Jeopardize Ovarian Suppression and Cycle Control? Abstract Book, VIIIth World Congress on Human Reproduction, Bali, Indonesia (1993)].

Other preparations have been described which contain an estrogenic and a gestagenic active ingredient and which generally are administered over 21 days in constant amounts in each individual dosage unit, in which the intake of this dosage unit that contains an estrogenic and gestagenic active ingredient precedes the intake of exclusively estrogen-containing dosage units (Ijzerman, U.S. Pat. No. 3,502,772: Pasquale, U.S. Pat. No. 4,921,843; Kuhl et al., EP-A 0 499 348). In the case of these preparations, the patient begins taking dosage units that contain only one estrogenic active ingredient, specifically at a dosage that lies below the ovulation-inhibiting dose of the estrogenic component, which can lead to follicular development, either as early as on the first cycle day (Kuhl) or at the earliest on the second cycle day (Pasquale). Follicular development is thought to be responsible for breakthrough ovulations (Chowdhury et al., "Escape" Ovulation in Women Due to the Missing of Low-Dose Combination Oral Contraceptive Pills, Contraception, 22: 241–247, 1980; Molloy, B. G. et al., "Missed Pill" Conception: Fact or Fiction? Brit. Med. J. 290, 1474–1475, 1985). Contraceptive protection is thus jeopardized. The risk of pregnancy is therefore high, especially in the case of intake errors below the 20 μg ethinylestradiol preparations.

The object of this invention is to make available a combination preparation with an estrogen content that is as low as possible in each individual dosage unit but also with a low total hormone content per administration cycle, whereby with high contraceptive reliability, an incidence of follicular development that is as low as possible and satisfactory cycle control with reliable avoidance of intracyclic menstrual bleeding such as breakthrough bleeding and "spottings" as well as as little amenorrhea as possible are to be achieved and undesirable side-effects are to be avoided.

This object is achieved by the provision of the above-indicated two-phase combination preparation, in which between the first and the second hormone component, 2 or 1 active ingredient-free daily units (placebos) are present or 2 or 1 blank pill days are indicated.

In the first phase, beginning with the first day of the cycle, a dosage unit that contains an estrogen in combination with a gestagenic component is administered daily over 23 or 24 days. Subsequent to these 23 or 24 daily dosage units, 2 or 1 active ingredient-free daily units are administered or 2 or 1 blank pill days are indicated. After that is the second phase, in which an estrogen is administered over 4, 3 or 2 days over the remaining period in the cycle, which preferably comprises 28 days.

In this case, the first phase which contains both estrogen and gestagen can also be structured in multiple stages in a way that is familiar to one skilled in the art.

When the combination preparation according to the invention is taken, the recruitment of the dominant follicle, which in the spontaneous cycle occurs during the first 6 days of the menstrual cycle, is already efficiently suppressed in the first administration cycle. Thus, with the combination preparation of this invention, follicular development can be suppressed as early as in the first intake cycle, and thus breakthrough ovulations can be avoided, thereby increasing contraceptive reliability.

This is of eminent importance mainly in the case of intake errors, namely especially with hormonal contraceptives with low daily ethinylestradiol dose amounts. Since, in the case of 25% of women who take the pill, intake errors (skipping dosage units or extending the interval between the daily intake of two dosage units to more than 24 hours) are known (Finlay, I. G.; Scott, M. B. G.: Patterns of Contraceptive Pill-taking in an Inner City Practice. Br. Med. J. 1986, 293: 601–602), the combination preparation according to the invention, if it is used as an ovulation-inhibiting agent, increases contraceptive reliability. This is true especially in the case of lowest-dosed preparations.

The increase in the number of dosage units that contain both estrogen and gestagen above the usual number of 21 days to 23 or 24 days produces an effective shortening of the pill-free interval, in which the selection of follicles occurs with conventional combination preparations as in a normal menstrual cycle, and thus follicular development results and increased endogenic estrogen is formed. These follicles lead to breakthrough ovulations, as already stated above. These breakthrough ovulations occur to an increased extent especially in the case of intake errors.

The subsequent administration of 2 or 1 hormone-free daily units or inclusion of 2 or 1 blank pill days as well as the subsequent phase, in which dosage units that contain only one estrogenic component as a hormonal active ingredient are administered daily over 4, 3 or 2 days, ensures withdrawal bleeding and produces in the subsequent administration cycle a reduced rate of intracyclic menstrual bleeding compared with conventional, low-dosed preparations.

According to a preferred embodiment of the invention, the estrogen of the first hormone component is selected from the group of compounds 17β-estradiol, ethinylestradiol and 17β-estradiol valerate and the gestagen is selected from the group of compounds gestodene, levonorgestrel, desogestrel, 3-ketodesogestrel, drospirenonene, cyproterone acetate, norgestimate and norethisterone and the estrogen of the second hormone component is selected from the group of compounds 17β-estradiol, ethinylestradiol and 17β-estradiol valerate.

According to another preferred variant of this invention, the estrogen of the first hormone component in each daily dosage unit is contained in a dose of 1.0 to 6.0 mg of 17β-estradiol, 0.015 to 0.025 mg of ethinylestradiol, 1.0 to 4.0 mg of 17β-estradiol valerate and the gestagen in each daily dosage unit is contained in a dose of 0.05 to 0.075 mg of gestodene, 0.05 to 0.125 mg of levonorgestrel, 0.06 to 0.15 mg of desogestrel, 0.06 to 0.15 mg of 3-ketodesogestrel, 1.0 to 3.0 mg of drospironenone, 1.0 to 2.0 mg of cyproterone acetate, 0.2 mg to 0.3 mg of norgestimate, 0.35 to 0.75 mg of norethisterone.

The second hormone component contains the estrogen in each daily dosage unit preferably in an amount of 1.0 to 6.0 mg of 17β-estradiol, 0.002 to 0.04 mg of ethinylestradiol, 1.0 to 4.0 mg of 17β-estradiol valerate.

According to an especially preferred embodiment, the second hormone component in each daily dosage unit contains, as estrogen, ethinylestradiol in an amount of 0.01 to 0.015 mg.

A preparation according to this invention contains a total of preferably 28 hormone daily units.

As an estrogen for both the first and the second hormone component, primarily ethinylestradiol is considered.

Of the above-mentioned gestagens for the second hormone component, gestodene is to be emphasized; also levonorgestrel is preferred.

17β-estradiol valerate, which can be contained as estrogen both in the first and in the second hormone component, is mentioned only as a possible representative of this 17β-estradiol ester; other such homologous esters can also be used as estrogenic components within the scope of this invention.

The following examples are used to explain this invention in more detail:

EXAMPLES

| Day | 1 | 2 | 3 | 4 | 5 | 6 | 7 | |
|---|---|---|---|---|---|---|---|---|
| Composition | C | C | C | C | C | C | C | |
| Day | 8 | 9 | 10 | 11 | 12 | 13 | 14 | |
| Composition | C | C | C | C | C | C | C | |
| Day | 15 | 16 | 17 | 18 | 19 | 20 | 21 | |
| Composition | C | C | C | C | C | C | C | |
| Day | 22 | 23 | 24 | 25 | 26 | 27 | 28 | |
| Composition | C | C | C | P | P | E | E | Example 1 |
| | C | C | P | P | E | E | E | Example 2 |
| | C | C | C | P | E | E | E | Example 3 |
| | C | C | P | E | E | E | E | Example 4 |

Day = Day of the menstrual cycle, day 1 is the first day of bleeding
C = combination of estrogen and gestagen (= first hormone component)
E = estrogen (= second hormone component)
P = placebo or indications of a blank pill day.

The dosage units are formulated conventionally using estrogen-/gestagen- and exclusively estrogen-containing tablets, pills, coated tablets, etc. of known adjuvants for production.

The active ingredient-free daily units are formulated exclusively from these adjuvants. Instead of 2 or 1 active ingredient-free daily units, indications can also be contained in the combination preparation according to the invention that signal (to the user) that the intake of the first hormone component is to be followed by a two- or one-day pause without the intake of each dosage unit before proceeding with the second hormone component with the four-, three- or two-day intake.

The combination preparation according to the invention is used in female contraception by administering the daily dosage units of the first hormone component over 23 or 24 days, beginning on day one of the menstrual cycle (first day of menstrual bleeding), a subsequent two- or one-day hormone pause, followed by 4, 3 or 2 daily dosage units that contain exclusively an estrogen (E), during a total of at least 28 days in the administration cycle. With this combination preparation, pronounced ovarian suppression without frequent follicle stimulation, as well as excellent cycle control in the case of low daily estrogen dosage, low total amounts of estrogen, and low total amounts of hormone per administration cycle can be achieved.

The advantages of this combination preparation (ovulation-inhibiting agent) according to the invention that is administered over generally 28 days compared to the previously described preparations, especially those with a daily ethinylestradiol dose of less than 30 μg and those with a prolonged pill-free interval, can be characterized as follows:

1. A significantly lower frequency of follicular development in the user. This means a lower risk of breakthrough ovulation and thus greater contraceptive reliability, especially in the case of intake errors.
2. The recruitment of the dominant follicle is suppressed as early as in the first cycle by extending the intake of the combination to 23 or 24 days.
3. The intake of 4, 3 or 2 daily estrogen dosage units each in connection with the administration of the 23- or 24-day combination dosage and the two- or one-day pause results in considerably improved cycle control and a lower incidence of side-effects, such as headaches, within the framework of the premenstrual syndrome.
4. Other clinical symptoms that are attributable to greatly fluctuating endogenic estrogen levels, such as, for example, breast tenseness, are reduced also clearly owing to the considerably greater ovarian suppression.
5. Better cycle control, specifically from the first intake cycle, results. Reliable breakthrough bleeding is ensured by the 1- or 2-day intake pause in connection with the administration of 23- or 24-day combination dosage and before the intake of 4, 3 or 2 daily estrogen dosage units each, and thus the rate of amenorrhea is reduced.
6. Improved cycle control and the very low incidence of amenorrhea results in higher compliance.

The formulation of an estrogen and a gestagen for the production of a combination preparation according to the invention is carried out completely analogously to the way already known for conventional oral contraceptives with a 21-day intake period of the active ingredients, such as, for example, Femovan® (ethinylestradiol/gestodene) or Microgynon® (ethinylestradiol/levonorgestrel). The formulation of the dosage units that contain only estrogen can also be carried out quite analogously to the way known for already obtained estrogen-containing agents that are intended for oral use, for example, Progynon C®.

A packing that contains a combination preparation according to the invention is also built up analogously to packings for already known oral contraceptives that are on the market, with the difference that, instead of the usual 21 dosage units that contain active components, now 23 or 24 such dosage units, which are indicated by 2 or 1 active ingredient-free daily units or 2 or 1 blank pill days, and another 4, 3 or 2 dosage units that contain only estrogen are present. As a packaging form for the combination preparation according to the invention, generally a conventional blister pack is used, but other packaging forms that are known for this purpose are also conceivable.

To determine equivalent-action amounts of ethinylestradiol and 17β-estradiol, on the one hand, and various gestagens such as gestodene, levonorgestrel, desogestrel and 3-ketodesogestrel, on the other hand, reference is made to the indications given in EP-A-0 253 607. Other details for determining dose equivalents of various gestagenic active ingredients are found in, for example, "Probleme der Dosisfindung: Sexualhormone [Problems of Dose Finding: Sex Hormones]"; F. Neumann et al., in "Arzneimittelforschung [Pharmaceutical Agent Research]" (Drug Research) 27, 2a, 296–318 (1977) as well as in "Aktuelle Entwicklungen in der hormonalen Kontrazeption [Current Developments in Hormonal Contraception]": H. Kuhl in "Gynäkologe [Gynecologist]" 25: 231–240 (1992).

We claim:

1. A pharmaceutical combination preparation with two hormone components that are manufactured physically separately in a packaging unit and that are intended for time-sequential oral administration, comprising a number of daily dosage units of a first and a second hormone component that are placed physically separately and individually removable in the packaging unit, wherein said first hormone component comprises, in combination, an estrogen preparation and a dosage effective to inhibit ovulation of a gestagen preparation, in either a one-stage or multi-stage structure; and said second hormone component consisting essentially of an estrogen preparation, whereby the first hormone component comprises 23 or 24 daily units and the second hormone component comprises 4, 3 or 2 daily units, and between these two hormone components, 2 or 1 active ingredient-free daily units are present or 2 or 1 blank pill days are indicated, and the total number of hormone daily units is equal to the total number of days of the desired cycle, but at least 28 days in length, and whereby the low effective estrogen content and low total hormone content provides high contraceptive reliability, low incidence of follicular development, and satisfactory cycle control, with reliable avoidance of intracyclic menstrual bleeding and undesirable side-effects.

2. A combination preparation according of claim 1, wherein the estrogen of the first hormone component is selected from the group consisting of 17β-estradiol, ethinylestradiol and 17β-estradiol valerate and the gestagen is selected from the group consisting of gestodene, levonorgestrel, desogestrel, 3-ketodesogestrel, drospironenone, cyproterone acetate, norgestimate and norethisterone and the estrogen of the second hormone component is selected from the group consisting of 17β-estradiol, ethinylestradiol and 17β-estradiol valerate.

3. A combination preparation of claim 2, wherein the estrogen of the first hormone component in each daily dosage unit is present in a dose of 1.0 to 6.0 mg of 17β-estradiol, 0.015 to 0.025 mg of ethinylestradiol or 1.0 to 4.0 mg of 17β-estradiol valerate;

and the gestagen in each daily dosage unit is present in a dose of 0.05 to 0.075 mg of gestodene, 0.05 to 0.125 mg of levonorgestrel, 0.06 to 0.15 mg of desogestrel, 0.06 to 0.15 mg of 3-ketodesogestrel, 1.0 to 3.0 mg of drospironenone, 1.0 to 2.0 mg of cyproterone acetate, 0.2 mg to 0.3 mg of norgestimate or 0.35 to 0.75 mg of norethisterone.

4. A combination preparation of claim 2, wherein the second hormone component in each daily dosage unit is present in an amount of 1.0 to 6.0 mg of 17β-estradiol, 0.002 to 0.04 mg of ethinylestradiol or 1.0 to 4.0 mg of 17β-estradiol valerate.

5. A combination preparation of claim 4, wherein the second hormone component in each daily dosage unit contains ethinylestradiol in an amount of 0.01 to 0.015 mg.

6. A combination preparation of claim 1, wherein the total number of hormone daily units and the active ingredient-free daily units or blank pill days is 28.

7. A method of inducing a contraceptive effect for female birth control, comprising administering a sequential daily dosage unit of a pharmaceutical combination preparation of claim 1, in the sequence set forth.

8. A method of claim 7, wherein each individual dosage unit has a very low effective estrogen content and a very low effective total hormone content per administration cycle, and whereby the low effective estrogen content and low total hormone content provides high contraceptive reliability, low incidence of follicular development, and satisfactory cycle control, with reliable avoidance of intracyclic menstrual bleeding and undesirable side-effects.

9. A method of claim 8, wherein the low effective estrogen content of the first hormone component in each daily dosage unit comprises 1.0 to 6.0 mg of 17β-estradiol, 0.015 to 0.025 mg of ethinylestradiol or 1.0 to 4.0 mg of 17β-estradiol valerate;

and the low effective gestagen content comprises 0.05 to 0.075 mg of gestodene, 0.05 to 0.125 mg of levonorgestrel, 0.06 to 0.15 mg of desogestrel, 0.06 to 0.15 mg of 3-ketodesogestrel, 1.0 to 3.0 mg of drospironenone, 1.0 to 2.0 mg of cyproterone acetate, 0.2 mg to 0.3 mg of norgestimate or 0.35 to 0.75 mg of norethisterone; and the low effective estrogen content of the second hormone component comprises 1.0 to 6.0 mg of 17β-estradiol, 0.002 to 0.04 mg of ethinylestradiol or 1.0 to 4.0 mg of 17β-estradiol valerate.

10. A pharmaceutical combination preparation of claim 1, whereby high contraceptive reliability, low incidence of follicular development, and satisfactory cycle control, with reliable avoidance of intracyclic menstrual bleeding and undesirable side-effects are provided.

* * * * *

UNITED STATES PATENT AND TRADEMARK OFFICE
CERTIFICATE OF CORRECTION

PATENT NO. : 5,980,940
DATED : November 9, 1999
INVENTOR(S) : Jurgen Spona; Bernd Dusterberg It is certified that error appears in the above-identified patent and that said Letters Patent is hereby corrected as shown below:

Column 7, claim 1,
Line 32, insert the term "active ingredient-free daily units, and/or blank pill days" after "the total number of hormone daily units,".

Signed and Sealed this

Ninth Day of October, 2001

Attest:

NICHOLAS P. GODICI
Attesting Officer
Acting Director of the United States Patent and Trademark Office